United States Patent
Ko et al.

(10) Patent No.: US 8,626,261 B2
(45) Date of Patent: Jan. 7, 2014

(54) ELECTRODE FOR A LIVING BODY AND DEVICE FOR DETECTING A BIO-SIGNAL

(75) Inventors: Byung-hoon Ko, Hwaseong-si (KR); Jong-pal Kim, Seoul (KR); Hyung-sok Yeo, Hwaseong-si (KR); Youn-ho Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 177 days.

(21) Appl. No.: 13/033,776

(22) Filed: Feb. 24, 2011

(65) Prior Publication Data

US 2012/0041292 A1  Feb. 16, 2012

(30) Foreign Application Priority Data

Aug. 16, 2010  (KR) .................. 10-2010-0078854

(51) Int. Cl.
*A61B 5/04*  (2006.01)
(52) U.S. Cl.
USPC ............ 600/391; 600/372; 600/392; 600/393
(58) Field of Classification Search
USPC .................... 600/372, 382, 386, 391–393
See application file for complete search history.

(56) References Cited

U.S. PATENT DOCUMENTS

| | | | |
|---|---|---|---|
| 4,398,545 A * | 8/1983 | Wilson | 607/152 |
| 5,511,553 A * | 4/1996 | Segalowitz | 600/508 |
| 5,578,065 A * | 11/1996 | Hattori et al. | 607/46 |
| 7,486,980 B2 * | 2/2009 | Lin et al. | 600/391 |
| 2006/0167353 A1 * | 7/2006 | Nazeri | 600/386 |
| 2007/0093705 A1 * | 4/2007 | Shin et al. | 600/372 |
| 2007/0285868 A1 * | 12/2007 | Lindberg et al. | 361/232 |

FOREIGN PATENT DOCUMENTS

| | | |
|---|---|---|
| JP | 3006112 | 10/1994 |
| JP | 2007-44208 | 2/2007 |
| JP | 2009-45122 | 3/2009 |
| KR | 10-2007-0043124 A | 4/2007 |
| KR | 10-2008-0113656 | 12/2008 |
| KR | 10-2009-0008786 | 1/2009 |
| KR | 10-2010-0025321 | 3/2010 |

* cited by examiner

*Primary Examiner* — Lee S Cohen
(74) *Attorney, Agent, or Firm* — NSIP Law

(57) ABSTRACT

Provided are an electrode for a living body and a device for detecting bio-signals using the electrode. The electrode includes an insulation sheet that has at least one via hole, an electrode unit formed in the at least one via hole, and a guiding unit for guiding the attachment of a signal processing unit.

18 Claims, 14 Drawing Sheets

ELECTRODE FOR A LIVING BODY AND DEVICE FOR DETECTING A BIO-SIGNAL

CROSS-REFERENCE TO RELATED APPLICATION(S)

This application claims the benefit under 35 U.S.C. §119(a) of Korean Patent Application No. 10-2010-0078854, filed on Aug. 16, 2010, in the Korean Intellectual Property Office, the entire disclosure of which is incorporated herein by reference for all purposes.

BACKGROUND

1. Field

The following description relates to electrodes for a living body and devices for detecting bio-signals, and more particularly, to electrodes for a living body which have a reduced size for improved user convenience and which are capable of stably acquiring fine signals, and to devices for detecting bio-signals using the electrodes.

2. Description of the Related Art

Recently, connected healthcare systems for detecting various bio-signals in daily life have been developed. For example, the detection of bio-signals may be used to improve accuracy and convenience of diagnosis, to help the telediagnosis of medical staff by providing health-related services through databases of personal health information, to deliver results of diagnosis/prescriptions, and the like. A living body is a type of conductor, and a number of minute electric currents are generated therein. Accordingly, an inner condition of a living body may be detected by detecting such minute electric currents or by detecting changes in electric currents with respect to external stimuli in the living body. Generally, various bio-signals such as electrocardiogram (ECG), electromyogram (EMG), electroencephalogram (EEG), galvanic skin resistance (GSR), electrooculography (EOG), body temperature, heartbeat, pulse, blood pressure, body movement, and the like, may be detected, and an electrode for a living body may be used to detect changes in such bio-signals.

An electrode for a living body that is attached to the skin of a user may act as a medium for connecting the living body of the user to a detecting system. This attached electrode may affect the quality of detected bio-signals and user convenience. In order for an electrode to be attached to the living body of a user and to detect bio-signals of the user at all times, various technical problems with respect to accuracy of detection, communication, power consumption, and the like, need to be addressed. In addition, the electrode should be easy to use.

Furthermore, an electrode that is attached to a living body as a wearable sensor should be miniaturized to be of small size and to be lightweight. A generally used electrode for a living body may be manufactured to be disposable based on performance and user convenience. When an electrode for a living body is attached to the skin of a user and the user moves for an extended period of time thereafter, it may be difficult to acquire accurate signals. For example, the accuracy of the signal may be affected due to weakened adhesiveness of the electrode attached to his or her body and/or evaporation of electrolytes.

SUMMARY

In one general aspect, there is provided an electrode for a living body for connecting the living body to a signal processing module, the electrode comprising an insulation sheet comprising at least one via hole, an electrode unit formed in the at least one via hole, and a guiding unit configured to guide the attachment of the signal processing unit to the electrode for a living body.

The guiding unit may comprise at least one protruding unit configured to guide the signal processing module to a location to which the signal processing module is to be attached.

The guiding unit may comprise an outer wall structure formed at edges of the insulation sheet.

The guiding unit may comprise an electrode-side combining unit that may be combined with the signal processing module.

The guiding unit may comprise an end portion configured to be inserted into a slot of the signal processing module.

The electrode-side combining unit may comprise at least one of a zip fastener, a hook/loop fastener, and a flexible magnet.

The guiding unit may comprise a folded structure for guiding the signal processing module to a location to which the signal processing module is to be attached.

The electrode unit may comprise a device contacting portion that is formed of a conductive and adhesive material on a surface of the insulation sheet and that contacts a terminal of the signal processing module, and a body contacting portion that is formed on the other surface of the insulation sheet and that is electrically connected to the device contacting portion.

An adhesive material may be applied to regions of the insulation sheet around a device contacting portion.

In another aspect, there is provided a device for detecting bio-signals, the device comprising an electrode for a living body, and a signal processing module, wherein the electrode for a living body comprises an insulation sheet comprising at least one via hole, an electrode unit formed in the at least one via hole, and a guiding unit for guiding attachment of the signal processing unit, and the signal processing module comprises a terminal corresponding to the electrode unit of the electrode for a living body.

The guiding unit may comprise at least one protruding unit configured to guide the signal processing module to a location to which the signal processing module is to be attached.

The guiding unit may comprise an outer wall structure formed at edges of the insulation sheet.

The guiding unit may comprise a combining unit that combines the electrode for a living body and the signal processing module.

The guiding unit may comprise an inserting portion, and the signal processing module may comprise a slot into which the inserting portion of the guiding unit is to be inserted.

The combining unit may comprise at least one of a zip fastener, a hook/loop fastener, and a flexible magnet.

The guiding unit may comprise a folded structure for guiding the signal processing module to a location to which the signal processing module is to be attached.

The electrode unit may comprise a device contacting portion that is formed of a conductive and adhesive material on a surface of the insulation sheet and that contacts a terminal of the signal processing module, and a body contacting portion that is formed on the other surface of the insulation sheet and is electrically connected to the device contacting portion.

An adhesive material may be applied to regions of the insulation sheet around the device contacting portion.

A silicon releasing agent may be applied onto the surface of the signal processing module, and the surface of the signal processing module may contact the electrode for a living body.

The signal processing module may further comprise an analog signal processing unit configured to process analog signals transmitted from the terminal, an analog to digital (A/D) converter configured to convert the analog signals to digital signals, and a digital signal processing unit configured to process the converted digital signals.

Other features and aspects will be apparent from the following detailed description, the drawings, and the claims.

Figure 1:
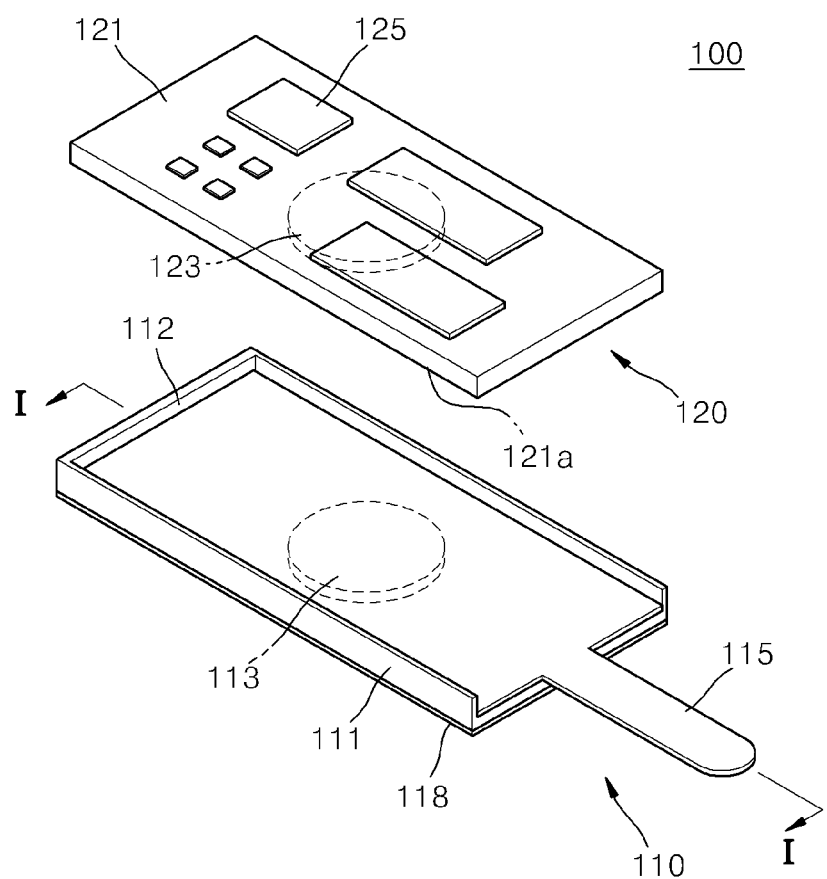
FIG. 1 is a diagram illustrating an example of a device for detecting bio-signals.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Figure 2:
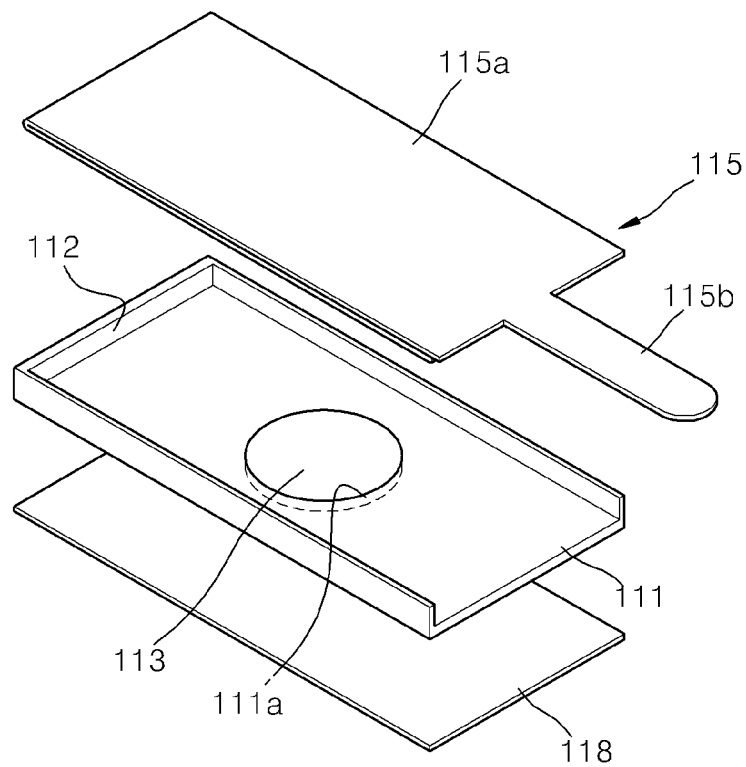
FIG. 2 is diagram illustrating an example of an exploded perspective view of an electrode for a living body, which may be employed by the device for detecting bio-signals of FIG. 1.
Figure 3:
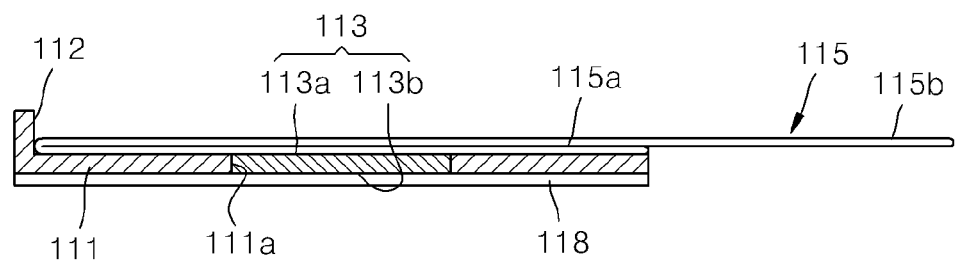
FIG. 3 is a diagram illustrating an example of cross-sectional view of the electrode for a living body of FIG. 2.

FIG. 1 illustrates an example of a device for detecting bio-signals. FIG. 2 illustrates an example of an exploded perspective view of an electrode for a living body, which may be employed by the device for detecting bio-signals of FIG. 1. FIG. 3 illustrates an example of a cross-sectional view of the electrode for a living body of FIG. 2.

Referring to FIG. 1, a device for detecting bio-signals 100 includes an electrode for a living body 110 and a signal processing module 120. The electrode for a living body 110 may be attached to a living body, and the signal processing module 120 may be attached to the electrode for a living body 110. For example, an electrolyte cream containing an electrolyte may be used to attach the electrode for a living body 110 to a living body. As an example, the electrolyte cream may be applied to the skin, and then the electrode for a living body 110 may be attached thereto.

Referring to FIGS. 1-3, the electrode for a living body 110 includes an insulation sheet 111, a guiding unit 112, an electrode unit 113, and first and second protection films 115 and 118.

In this example, the insulation sheet 111 is a flexible flat panel member, and a via hole 111a is formed near the center of the insulation sheet 111. For example, the insulation sheet 111 may be formed of a nonconductive material or an insulation material. For example, the insulation sheet 111 may be formed of an insulation resin, an insulation fiber, paper, a combination thereof, and the like. The rectangular shape of the insulation sheet 111 as shown in FIG. 2 is merely for purposes of example, and it should be appreciated that the insulation sheet 111 may be formed of various shapes including circular shapes, polygonal shapes, and the like. An electrode unit 113 may be inserted into the via hole 111a. Although the via hole 111a has a circular shape in FIG. 2, the via hole 111 may be formed of various shapes, for example, elliptical shapes, rectangular shapes, polygonal shapes, and the like.

In the examples of FIGS. 1-3, the via hole 111a is formed at or near the center of the insulation sheet 111. However, the device is not limited thereto, and it should be understood that one or more via holes 111a may be located at any desired location of the insulation sheet 111.

The guiding unit 112 may be formed as an outer wall structure protruding at edges of the insulation sheet 111. For example, the guiding unit 112 may be formed by folding edges of the insulation sheet 111 or by attaching separately formed outer walls to edges of the insulation sheet 111. In this example, the guiding unit 112 is formed at three edges of the insulation sheet 111 except for the edge of the insulation sheet 111 at which a tab portion 115b protrudes from the first protection film 115 out of the insulation sheet 111. It should be appreciated that the guiding unit 112 is not limited to this design. For example, the guiding unit 112 may be formed at at least one edge of the insulation sheet 111 other than the edge of the insulation sheet 111 at which the tab portion 115b protrudes from the first protection film 115 out of the insulation sheet 111. As another example, if the insulation sheet 111 has a circular shape or a polygonal shape, the guide unit 112 may be correspondingly formed at some or all of the edges of the circular shape or the polygonal shape. The outer wall structure is an example of protruding portions for defining the location of the signal processing unit 120, and the guiding unit 112 may provided on an inner side of the insulation sheet 111.

As described below with reference to FIGS. 5A through 5D, the guiding unit 112 guides the attachment of the signal processing unit 120 to be attached to the electrode for a living body 110. Furthermore, the guiding unit 112 may prevent the electrode for a living body 110 and/or the signal processing module 120 from being pushed with the first protection film 115 while the first protection film 115 is being removed.

The electrode unit 113 may transmit minute electric currents in a living body to the signal processing unit 120. In this example, the electrode unit 113 includes a device contacting portion 113a and a living body contacting portion 113b. For example, the device contacting portion 113a and the living body contacting portion 113b may be formed of a conductive and adhesive material. Because the device contacting portion 113a has an adhesiveness, the device contacting portion 113a may be attached to the bottom surface (121a of FIG. 1) of the signal processing module 120 and may maintain valid adhesiveness. Any desired conductive and adhesive materials may be used. As a non-exhaustive example, a hydro gel may be used.

The device contacting portion 113a and the living body contacting portion 113b may be connected to each other as a single body via the via hole 111a. For example, the device contacting portion 113a and the living body contacting portion 113b may be formed by molding melted or liquid hydro gel on both surfaces of the insulation sheet 111. For example, the device contacting portion 113a and the living body contacting portion 113b may be formed simultaneously by spraying liquid hydro gel to regions around the via hole 111a on both surfaces of the insulation sheet 111 and compressing the applied hydro gel using molds at both surfaces of the insulation sheet 111. Although FIG. 2 illustrates an example in which the device contacting portion 113a and the living body contacting portion 113b of the electrode unit 113 are placed in the via hole 111a, the device is not limited thereto.

For example, the device contacting portion 113a and the living body contacting portion 113b may be formed to spread on regions on both surfaces of the insulation sheet 111 around the via hole 111. Because the electrode unit 113 is attached to the signal processing module 120 by an adhesive, the device contacting portion 113a may be formed to have a thin planar shape, and thus the overall thickness of the electrode unit 113 may be reduced. Furthermore, because the device contacting portion 113a and a terminal 123 of the signal processing module 120 simply contact surface by surface to each other, the thickness of the signal processing module 120 may be reduced. Furthermore, a signal transmission process from the skin to a circuit may be reduced because the thickness of the signal processing module 120 is reduced. Dynamic noises may also be reduced.

The insulation sheet 111 and the electrode unit 113 may be flexibly deformed, and thus may be easily and adaptively attached to a location. To improve a mechanical combination between the electrode for a living body 110 and the signal processing module 120 for providing a stable detecting environment, an adhesive material may be applied to the edges of the top surface of the insulation sheet 111 around the device contacting portion 113a. As another example, an adhesive material may be applied to the edges of the bottom surface of the insulation sheet 111 around the living body contacting portion 113b.

In this example, the first protection film 115 includes a protection portion 115a and the tab portion 115b, which is an extended portion of the protection portion 115a. For example, the protection portion 115a may be formed to completely cover the surface of the insulation sheet 111 contacting the signal processing module 120. The protection portion 115a may protect an adhesive applied to the surface of the electrode for a living body 110 contacting the signal processing module 120 to maintain the performance of the adhesive. For example, the protection portion 115a may have a double layer structure formed by folding a single protection film. In this example, an upper layer of the protection portion 115a toward the signal processing module 120 may extend and form the tab portion 115b.

The second protection film 118 may protect an adhesive applied to the surface of the electrode for a living body 110 contacting a living body to maintain the performance of the adhesive. For example, the second protection film 118 may be formed to completely cover the opposite surface of the surface of the insulation sheet 111 that contacts the signal processing module 120.

Referring back to FIG. 1, the signal processing unit 120 includes a substrate 121, on which electronic parts 125 for processing signals are mounted, and the terminal 123 that contacts the electrode unit 113 of the electrode for a living body 110.

For example, the substrate 121 may have a rectangular shape housed in the guiding unit 112, which forms the outer wall structure of the insulation sheet 111. As another example, if the guiding unit 112 is formed to have a circular shape or a polygonal shape, the substrate 121 may be formed to have a circular shape or a polygonal shape in correspondence to the shape of the guiding unit 112. As another example, if the guiding unit 112 is formed on the middle of the insulation sheet 111, grooves into which the guiding unit 112 is inserted may be formed in the bottom surface 121a of the substrate 121.

In some examples, the insulation sheet 111 may include a plurality of via holes 111a that each include a respective electrode unit 113 formed therein. In addition, the signal processing unit 120 may include a plurality of terminals 123 at locations corresponding to the locations of the plurality of electrode units 113.

The substrate 121 may be formed as a flexible circuit board, which may be flexibly deformed, and may be deformed in correspondence to deformation of the electrode for a living body 110. As another example, the substrate 121 may be formed of a rigid material. If the substrate 121 is formed of a rigid material, the terminal 123 may be formed to have flexibility, such that the terminal 123 may move in correspondence to a deformation of the electrode for a living body 110.

The terminal 123 may be exposed on the bottom surface 121a of the substrate 12a, and the signal processing module 120 may be attached to the electrode for a living body 110, such that the bottom surface 121a of the substrate 121 is located on the device contacting portion 113a. For example, a silicon releasing agent may be applied onto the bottom surface 121a of the substrate 121. If the adhesive applied to the electrode for a living body 110 has strong adhesive power, the signal processing module 120 may be damaged when the electrode for a living body 110 is removed. Therefore, the silicon releasing agent may prevent the signal processing module 120 from being damaged by easing the removal of the electrode for a living body 110.

Because the electrode unit 113 and the terminal 123 may contact each other via flat surfaces, resistance between the electrode unit 113 and the terminal 123 may be reduced due to a surface contact. Therefore, even minute electric currents in a living body may be effectively transmitted to the terminal 123 of the signal processing module 123, and thus, signal-to-noise (S/N) ratio may be reduced.

Because the device contacting portion 113a of the electrode unit 113 has an adhesive power, the electrode unit 113 may be kept attached to the signal processing module 120 without a separate fixing mechanism.

Figure 4:
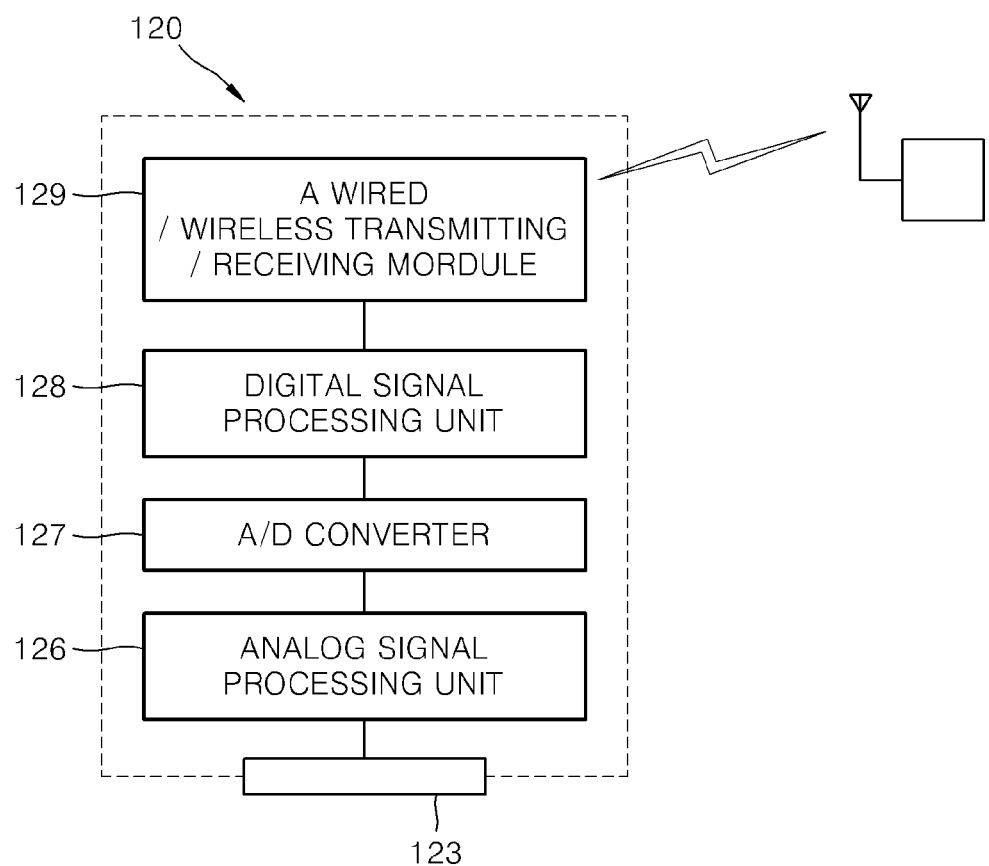
FIG. 4 is a diagram illustrating an example of a signal processing module.

FIG. 4 illustrates an example of a signal processing module. Referring to FIG. 4, signal processing module 120 includes an analog signal processing unit 126, an analog to digital (A/D) converter 127, a digital signal processing unit 128, and a wired/wireless transmitting/receiving module 129, which may be connected to the terminal 123 of the bottom surface 121a of the substrate 121 in the order stated, or in a different order.

The analog signal processing unit 126 may amplify and/or filter minute electric currents transmitted from the terminal 123 such as analog signals and may transmit the amplified or filtered analog signals to the A/D converter 127. The A/D converter 127 converts the transmitted analog signals to digital signals and may transmit the converted digital signals to the digital signal processing unit 128. The digital signal processing unit 128 may process the converted digital signals, for example, the digital signal processing unit 128 may process the converted digital signals according to a programmed algorithm. The wired/wireless transmitting/receiving module 129 may transmit the digital signals processed by the digital signal processing unit 128 to an external device. For example, the wired/wireless transmitting/receiving module 129 may transmit the digital signals by a wired and/or a wireless connection, and may receive an operating signal from the external device.

As described above, the signal processing module 120 may be connected to an external device by wire or wirelessly, and may transmit information regarding bio-signals of a wearer, such as electrocardiogram (ECG), electromyogram (EMG), electroencephalogram (EEG), galvanic skin resistance (GSR), while being attached to a living body. As another example, a memory (not shown) may be disposed in the signal processing module 120 instead of the wired/wireless transmitting/receiving module 129, and thus digital signals processed by the digital signal processing unit 128 may be stored in the memory.

FIGS. 5A through 5D illustrate examples of a device for detecting bio-signals in which the signal processing module of FIG. 4 is attached to the electrode for a living body of FIG. 2.

Figure 5A:
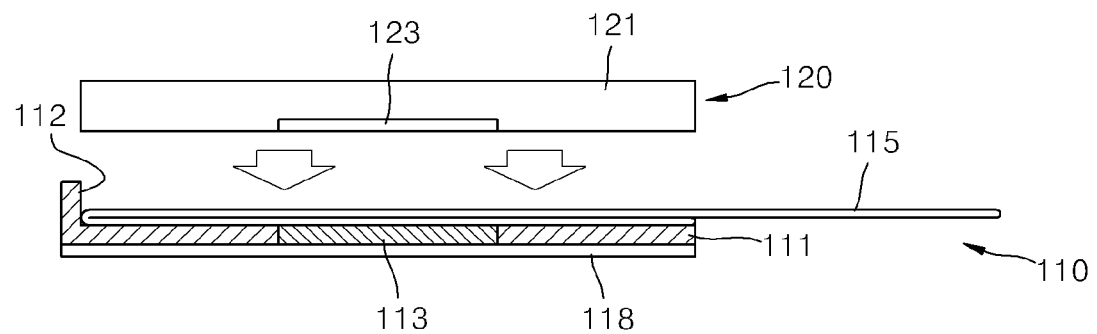
FIGS. 5A through 5D are diagrams illustrating examples of a device for detecting bio-signals in which the signal processing module of FIG. 4 is attached to the electrode for a living body of FIG. 2.
Figure 5B:
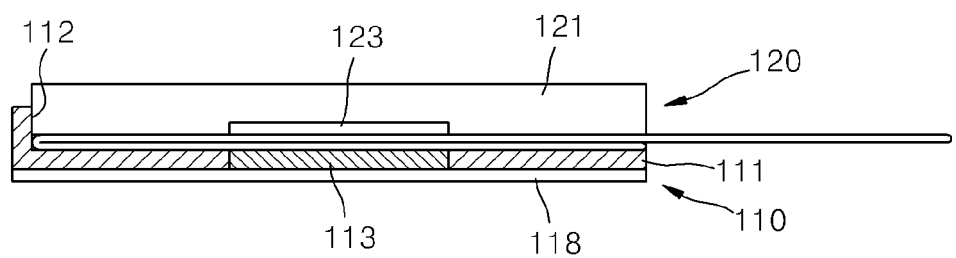

Referring to FIGS. 5A and 5B, the signal processing module 120 may be aligned with the guiding unit 112 of the electrode for a living body 110 and may be attached onto the electrode for a living body 110. For example, the guiding unit 112 may guide the signal processing module 120 such that the electrode unit 113 of the electrode for a living body 110 and the terminal 123 of the signal processing module 120 are aligned. Because the electrode for a living body 110 and the signal processing module 120 may be formed of flexible materials, alignment between the signal processing module 120 and the electrode for a living body 110 may be easily dislocated while the signal processing module 120 is being attached to the electrode for a living body 110. However, in the device described herein, because the electrode unit 113 and the terminal 123 are aligned with each other based on the guiding unit 112, an electrical path of bio-signals detected by the electrode for a living body 110 may be secured, and the impedance between the electrode for a living body 110 and the signal processing module 120 may be reduced.

Figure 5C:
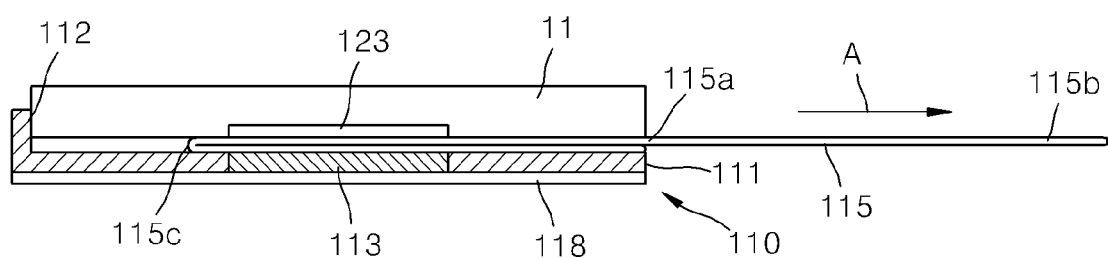

Referring to FIG. 5C, while the signal processing module 120 is aligned with the guiding unit 112 of the electrode for a living body 110, the tab portion 115b of the first protection film 115 may be pulled. In this example, as the tab portion 115b is pulled, the upper layer of the protection portion 115a is pulled out, and an edge 115c of the first protection film 115 is separated from the top surface of the insulation sheet 111. Accordingly, as the edge 115c of the first protection film 115 is sequentially pulled out from the insulation sheet 111, the first protection film 115 may be removed while the signal processing module 120 is arranged on the electrode for a living body 110. In this example, because the electrode for a living body 110 and the signal processing module 120 are formed of flexible materials, the electrode for a living body 110 and/or the signal processing module 120 may be pushed with the first protection film 115 while the first protection film 115 is being removed. In this example, the guiding unit 112 prevents the electrode for a living body 110 or the signal processing module 120 from being pushed by the first protection film 115 while the first protection film 115 is being removed.

Figure 5D:
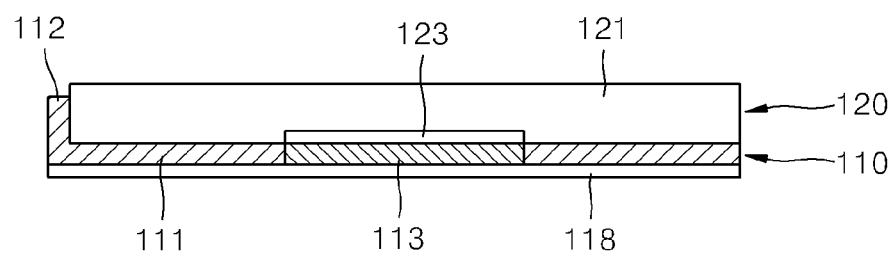

Accordingly, when the first protection film 115 is removed from the electrode for a living body 110, the signal processing module 120 may directly contact and may be adhered to the electrode for a living body 110 as shown in FIG. 5D.

It should be appreciated that the electrode for a living body 110 and the signal processing module 120 may be combined before or after the electrode for a living body 110 is attached to a living body. For example, if the electrode for a living body 110 and the signal processing module 120 are combined after the electrode for a living body 110 is attached to a living body, the second protection film 118 may be omitted from FIGS. 5A through 5D, and the electrode for the living body 110 may be placed directly in contact with a living body. Accordingly, the device for detecting bio-signals 100 may be placed in direct contact with a living body.

The device for detecting bio-signals 100 resolves mechanical combinations of the electrode for a living body 110 and the signal processing module 120 by using a conductive adhesive. Therefore, the overall thickness of the device for detecting bio-signals 100 may be reduced, and user convenience may be improved by easily combining the electrode for a living body 110 and the signal processing module 120 using the guiding unit 112.

Although the example of FIGS. 1-5 illustrate a case in which only one electrode unit 113 is formed in the electrode for a living body 110, it should be appreciated that the bio-signal sensing device may include a plurality of electrode units 113.

Figure 6:
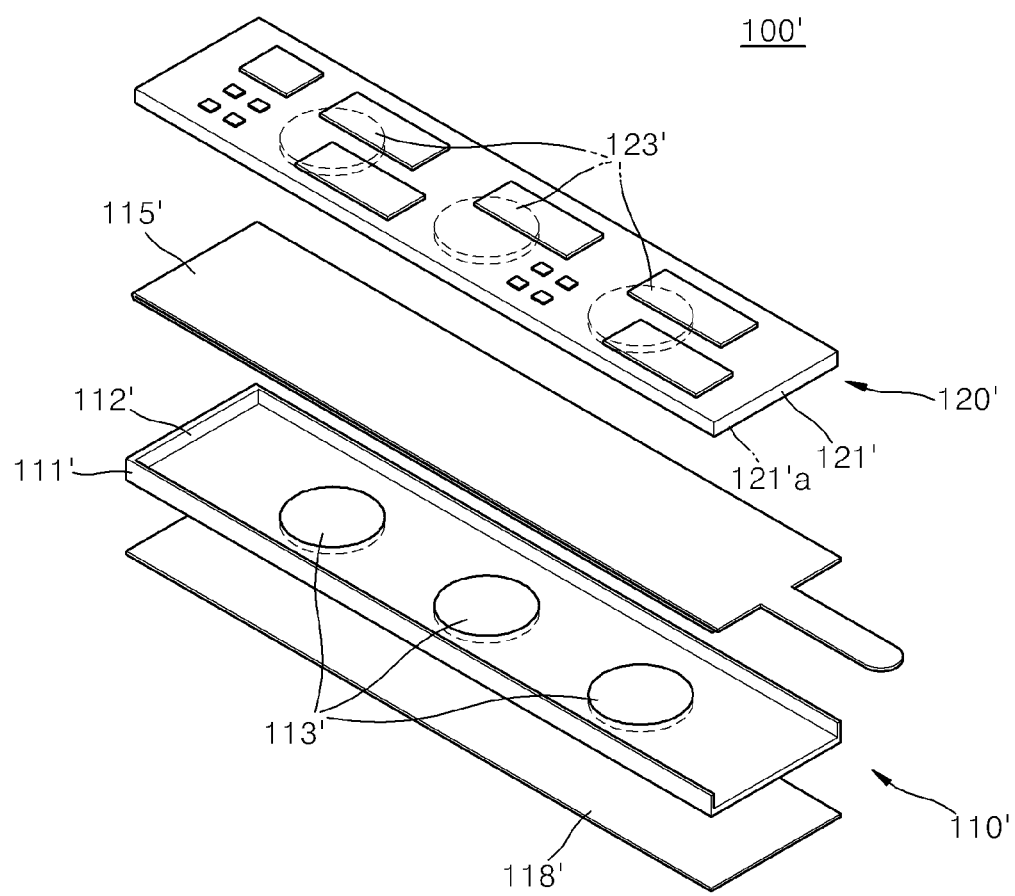
FIG. 6 is a diagram illustrating an example of a device for detecting bio-signals according to a modification of the device of FIG. 1.

FIG. 6 illustrates an example of a device for detecting bio-signals according to a modification of the device of FIG. 1. Referring to FIG. 6, device for detecting bio-signals 100' includes an electrode for a living body 110' that includes a plurality of electrode units 113' for detecting changes at a plurality of locations. In this example, a plurality of terminals 123' are formed in a signal processing module 120'. As the number of electrode units 113' and terminals 123' increase, it may be more difficult to combine the electrode for a living body 110' and the device for detecting bio-signals 100', which are flexible, in precise alignment. However, the guiding unit 112 may enable precise alignment between the plurality of terminals 123' and the plurality of electrode units 113' even when a plurality of electrode units and terminals are used.

The device for detecting bio-signals 100' is substantially the same as the device for detecting bio-signals 100 of FIG. 1 except that the plurality of electrode units 113' are formed in the electrode for a living body 110' and the plurality of terminals 123' are formed in the signal processing module 120'.

Figure 7:
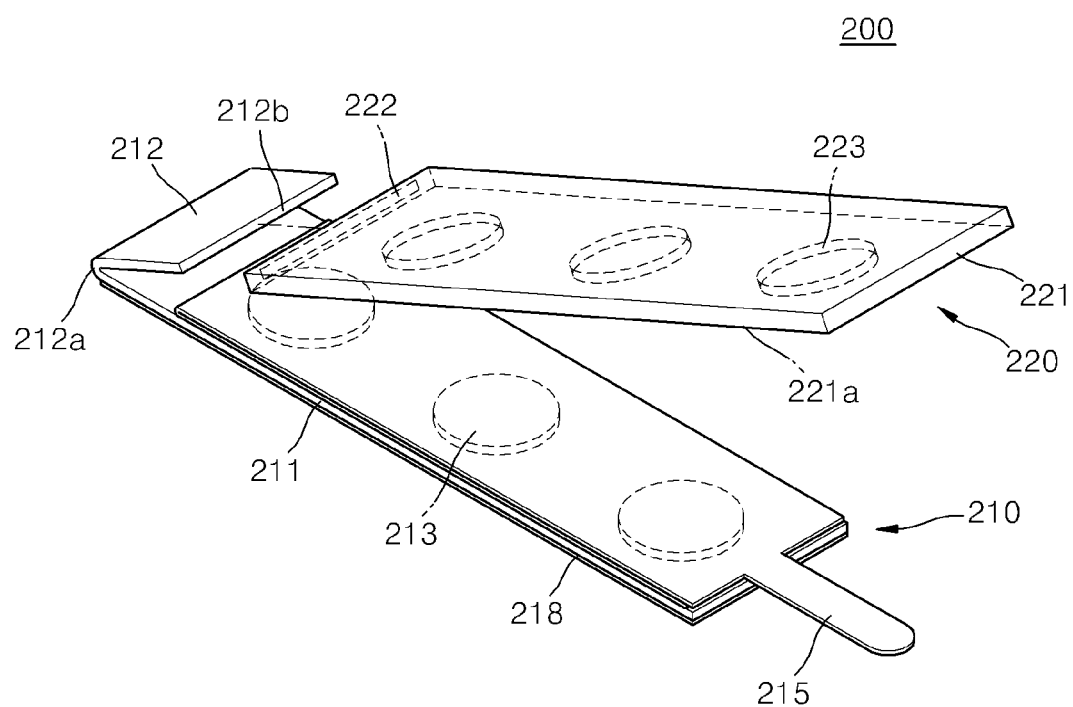
FIG. 7 is a diagram illustrating another example of a device for detecting bio-signals.
Figure 8:
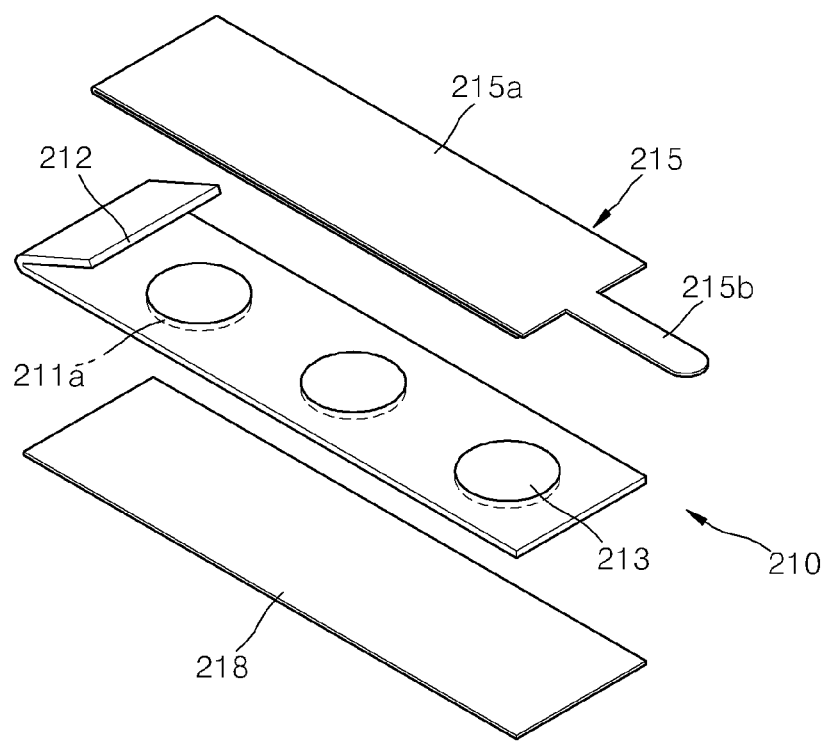
FIG. 8 is diagram illustrating an example of an exploded perspective view of an electrode for a living body, which may be employed by the device for detecting bio-signals of FIG. 7.

FIG. 7 illustrates another example of a device for detecting bio-signals, and FIG. 8 illustrates an example of an exploded perspective view of an electrode for a living body, that may be employed by the device for detecting bio-signals of FIG. 7.

Referring to FIGS. 7 and 8, device for detecting bio-signals 200 includes an electrode for a living body 210 and a signal processing module 220. In this example, the electrode for a living body 210 includes an insulation sheet 211, a guiding unit 212, an electrode unit 213, and first and second protection films 215 and 218. Also in this example, the signal processing module 220 includes a substrate 221, terminals 223 contacting the electrode unit 213 of the electrode for a living body 210, and a module-side combining unit 222, which is combined with the guiding unit 212. Components of the device for detecting bio-signals 200 other than the electrode for a living body 210 and the signal processing module 220 are substantially the same as the corresponding components stated in the previous examples, and thus, further description thereof is omitted here.

The insulation sheet 211 is a flexible flat panel member, in which a plurality of via holes 211a are formed. For example, the insulation sheet 211 may be formed of a nonconductive material or an insulation material. For example, the insulation sheet 211 may be formed of an insulation resin, an insulation fiber, paper, a combination thereof, and the like.

In this example, the guiding unit 212 is formed at an edge of the insulation sheet 211, and is folded along a predetermined border 212a. The guiding unit 212 may be a portion of the insulation sheet 211 or may be separately provided and attached to an edge of the insulation sheet 211. The border 212a along which the guiding unit 212 is folded may be determined in advance, such that the signal processing module 220 may be precisely attached to a location on the electrode for a living body 210. The border 212a may be marked, and may be pre-processed such that the guiding unit 212 may be easily folded. A portion of the guiding unit 212 including an edge 212b may become an inserting portion that may be inserted into the module-side combining unit 222 of the signal processing module 220.

The slot-type module-side combining unit 222, into which the guiding unit 212b of the guiding unit 212 may be inserted, is formed in the substrate 221 of the signal processing module 220. For example, the module-side combining unit 222 may be formed of a flexible material or a rigid material. The slot-type module-side combining unit 222 and the inserting portion of the guiding unit 212 are examples of fasteners that may be used to attach the electrode for a living body 210 and the signal processing module 220. Accordingly, the electrode for a living body 210 and the signal processing module 220 may be easily attached and detached.

FIGS. 9A through 9D illustrate examples of a device for detecting bio-signals in which a signal processing module is attached to the electrode for a living body of FIG. 8.

Figure 9A:
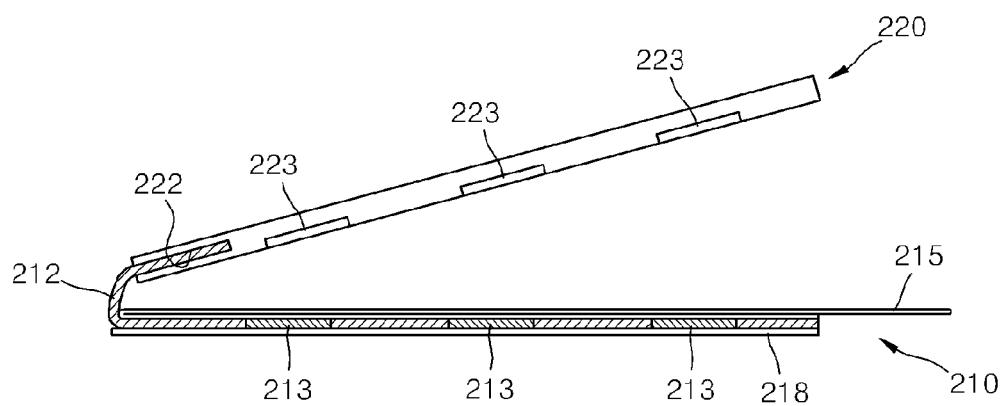
FIGS. 9A through 9D are diagrams illustrating examples of a device for detecting bio-signals in which a signal processing module is attached to the electrode for a living body of FIG. 8.
Figure 9B:
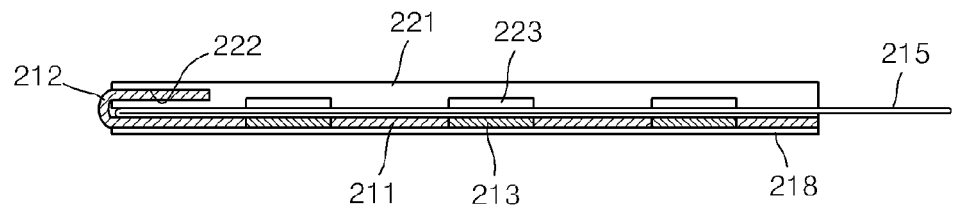

Referring to FIGS. 9A and 9B, a portion of the guiding unit 212 of the electrode for a living body 210 is inserted to the module-side combining unit 222 of the signal processing module 220. In this example, the guiding unit 212 is folded, such that the signal processing module 220 is aligned with the electrode for a living body 210. For example, the guiding unit 212 not only guides the electrode unit 213 of the electrode for a living body 210 and the terminal 223 of the signal processing module 220 to be precisely aligned, but also functions as an electrode-side combining unit which stably attaches the signal processing module 220 to the electrode for a living body 210.

Figure 9C:
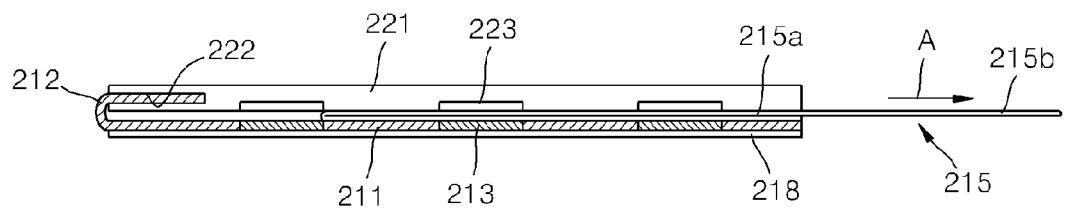

Referring to FIG. 9C, while the signal processing module 220 is aligned with the guiding unit 212 of the electrode for a living body 210, a tab portion 215b of the first protection film 215 may be pulled. As the tab portion 215b is pulled, the upper layer of a protection portion 215a is pulled out, and thus, the first protection film 215 may be removed. In this example, the guiding unit 212 prevents the electrode for a living body 210 or the signal processing module 220 from being pushed with the first protection film 215 while the first protection film 215 is being removed.

Figure 9D:
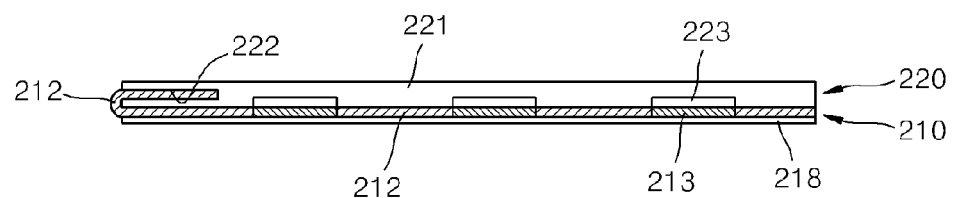

Accordingly, when the first protection film 215 is removed from the electrode for a living body 210, the signal processing module 220 may directly contact and may be adhered to the electrode for a living body 210 as shown in FIG. 9D. For example, the second protection film 218 may be removed and the device for sensing bio-signals 200 may be attached to a living body. As another example, if the electrode for a living body 210 is already attached to a living body before the signal processing module 220 is attached, the second protection film 218 may be omitted.

In this example, the electrode for a living body 210 and the signal processing module 220 may be attached to each other via an adhesive material applied on the electrode unit 213, and the guiding unit 212 may combine the electrode for a living body 210 and the signal processing module 220. As a result, the signal processing module 220 may be more stably attached to the electrode for a living body 210.

Figure 10:
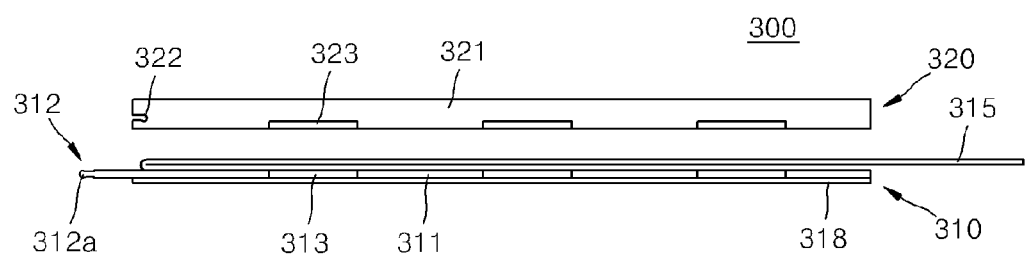
FIG. 10 is a diagram illustrating another example of a device for detecting bio-signals.

FIG. 10 illustrates another example of a device for detecting bio-signals. Referring to FIG. 10, device for detecting bio-signals 300 includes an electrode for a living body 310 and a signal processing module 320. In this example, the electrode for a living body 310 includes an insulation sheet 311, a guiding unit 312, an electrode unit 313, and first and second protection films 315 and 318. In this example, the signal processing module 320 includes a substrate 321, terminals 323 contacting the electrode unit 313 of the electrode for a living body 310, and a module-side combining unit 322, which may be combined with the guiding unit 312. Components of the device for detecting bio-signals 300 other than structures for guiding and combining the electrode for a living body 310 and the signal processing module 320 are substantially the same as the corresponding components stated in the previous examples, and thus, further description thereof is omitted here.

For example, the insulation sheet 311 may be formed of a nonconductive material or an insulation material. For example, the insulation sheet 311 may be formed of an insulation resin, an insulation fiber, paper, a combination thereof, and the like. In this example, the guiding unit 312 extends from an edge of the insulation sheet 311, and an edge 312a of the guiding unit 312 may be a convex zip fastener. In this example, the guiding unit 312 functions as an electrode-side combining unit as well as guiding the signal processing unit 320 to be attached to an accurate location on the electrode for a living body 310. For example, the guiding unit 312 may be formed by molding an edge of the insulation sheet 311 or may be separately formed and attached to an edge of the insulation sheet 311. The module-side combining unit 322, which may be a concave zip fastener corresponding to the guiding unit 312a of the guiding unit 312, may be formed at an edge of the substrate 321 of the signal processing module 320. The shape of the guiding unit 312a of the guiding unit 312 and the shape of the module-side combining unit 322 may be reversed. The guiding unit 312 may be folded or bent. The locations and sizes of the guiding unit 312 and the module-side combining unit 322 may be determined in advance for precise alignment between the electrode unit 313 of the electrode for a living body 310 and the terminal 323 of the signal processing module 320.

Figure 11A:
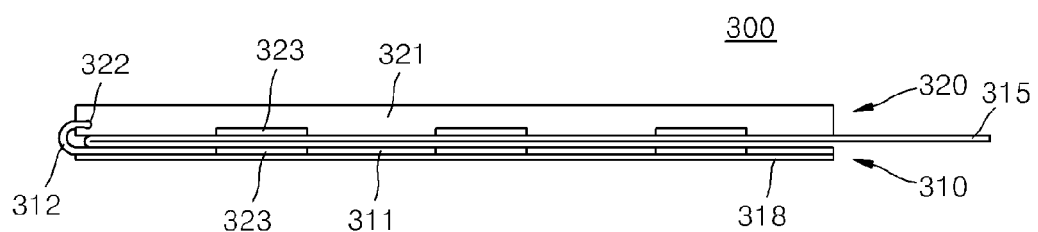
FIGS. 11A through 11C are diagrams illustrating examples of a device for detecting bio-signals in which a signal processing module is attached to the electrode for a living body of FIG. 10.
Figure 11B:
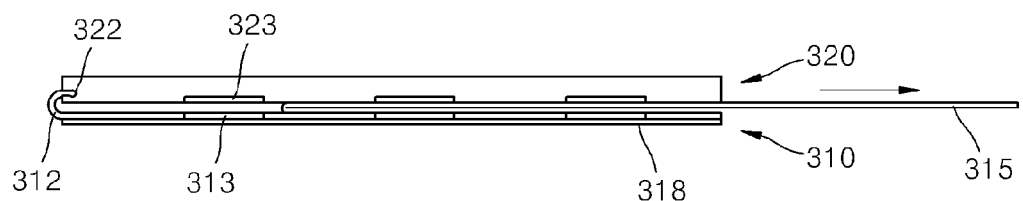
Figure 11C:
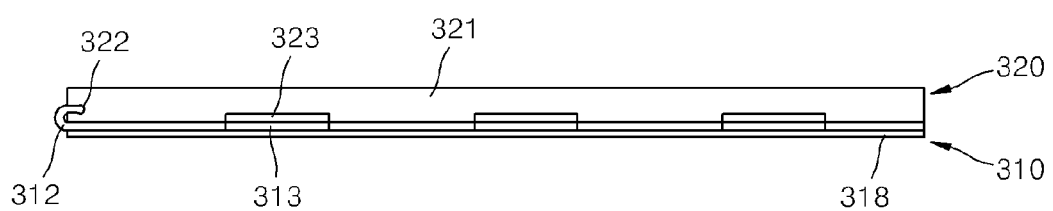

FIGS. 11A through 11C illustrate examples of a device for detecting bio-signals in which a signal processing module is attached to the electrode for a living body of FIG. 10.

Referring to FIG. 11A, an edge of the guiding unit 312 of the electrode for a living body 310 is inserted into the module-side combining unit 322 of the signal processing module 320, and the guiding unit 312 is folded, such that the signal processing module 320 is aligned with the electrode for a living body 310. In this example, the guiding unit 312 not only guides the electrode unit 313 of the electrode for a living body 310 and the terminal 323 of the signal processing module 320 to be precisely aligned, but also functions as an electrode-side combining unit which stably attaches the signal processing module 320 to the electrode for a living body 310.

Referring to FIG. 11B, while the signal processing module 320 is aligned with the guiding unit 312 of the electrode for a living body 310, the first protection film 315 may be pulled and removed. Accordingly, when the first protection film 315 is removed from the electrode for a living body 310, the signal processing module 320 may directly contact and may be adhered to the electrode for a living body 310 as shown in FIG. 11C. For example, the second protection film 318 may be removed and the device for sensing bio-signals 200 may be attached to a living body. As another example, if the electrode for a living body 310 is already attached to a living body before the signal processing module 320 is attached, the second protection film 318 may be omitted.

Figure 12:
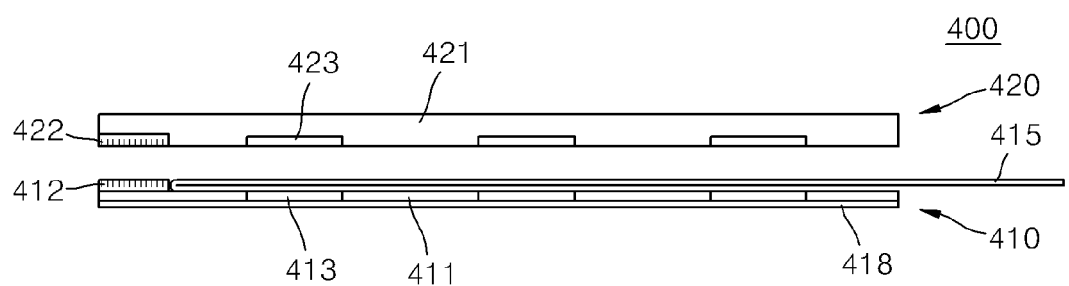
FIG. 12 is a diagram illustrating another example of a device for detecting bio-signals.

FIG. 12 illustrates another example of a device for detecting bio-signals. Referring to FIG. 12, device for detecting bio-signals 400 includes an electrode for a living body 410 and a signal processing module 420. In this example, the electrode for a living body 410 includes an insulation sheet 411, a guiding unit 412, an electrode unit 413, and first and second protection films 415 and 418. In this example, the signal processing module 420 includes a substrate 421, terminals 423 contacting the electrode unit 413 of the electrode for a living body 410, and a module-side combining unit 422, which is combined with the guiding unit 412. Components of the device for detecting bio-signals 400 other than structures for guiding and combining the electrode for a living body 410 and the signal processing module 420 are substantially the same as the corresponding components stated in the previous examples, and thus, further description thereof is omitted here.

For example, the insulation sheet 411 may be formed of a nonconductive material or an insulation material. For example, the insulation sheet 411 may be formed of an insulation resin, an insulation fiber, paper, a combination thereof, and the like.

In this example, the guiding unit 412 is formed at edges of the top surface of the insulation sheet 411, and may be a hook/loop fastener, that is, a VELCRO® type member. The guiding unit 412 may function as an electrode-side combining unit as well as guiding the signal processing unit 420 to be attached to an accurate location on the electrode for a living body 410. Furthermore, the module-side combining unit 422, which may be a hook/loop fastener corresponding to the hook/loop fastener of the guiding unit 412, may be formed on edges of the bottom surface of the substrate 421 of the signal processing module 420. For example, the guiding unit 412 may be a hook fastener and the module-side combining unit 422 may be a loop fastener, or vice versa. Locations of the guiding unit 412 and the module-side combining unit 422 may be determined, such that the electrode unit 413 of the electrode for a living body 410 and the terminal 422 of the signal processing module 420 may be precisely aligned. For example, a plurality of the guiding units 412 and a plurality of the module-side combining units 422 may be arranged. The locations of the guiding unit 412 and the module-side combining unit 422 are not limited to edges of the top surface of the insulation sheet 411 and edges of the bottom surface of the substrate 421, respectively. It should be appreciated that the guiding unit 412 and the module-side combining unit 422 may be arranged on various locations.

Figure 13:
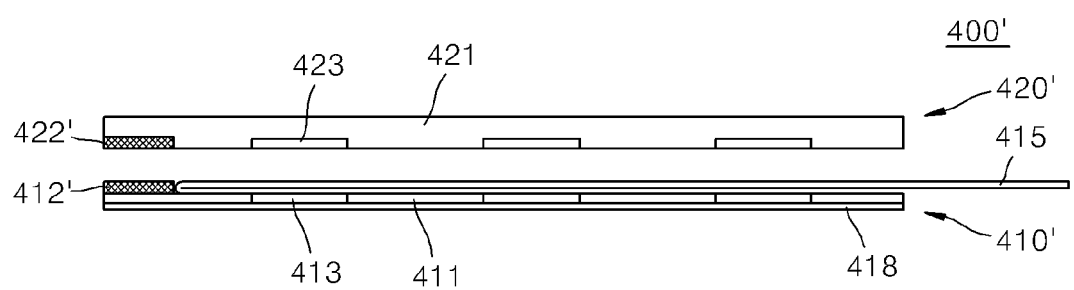
FIG. 13 is a diagram illustrating an example of a device for detecting bio-signals according to a modification of the device of FIG. 12.

Although the present example illustrates a case in which the guiding unit 412 and the module-side combining unit 422 are hook/loop fasteners, that is, VELCRO® type members, it is merely an example, and various modifications may be made thereto. FIG. 13 illustrates an example of a device for detecting bio-signals according to a modification of the device of FIG. 12. In the device for detecting bio-signals 400', a guiding unit 412' and a module-side combining unit 422' are formed of magnets, and thus an electrode for a living body 410' and a signal processing module 420' are magnetically combined. For example, the magnets constituting the guiding unit 412' and the module-side combining unit 422' may be flexible magnets.

Figure 14:
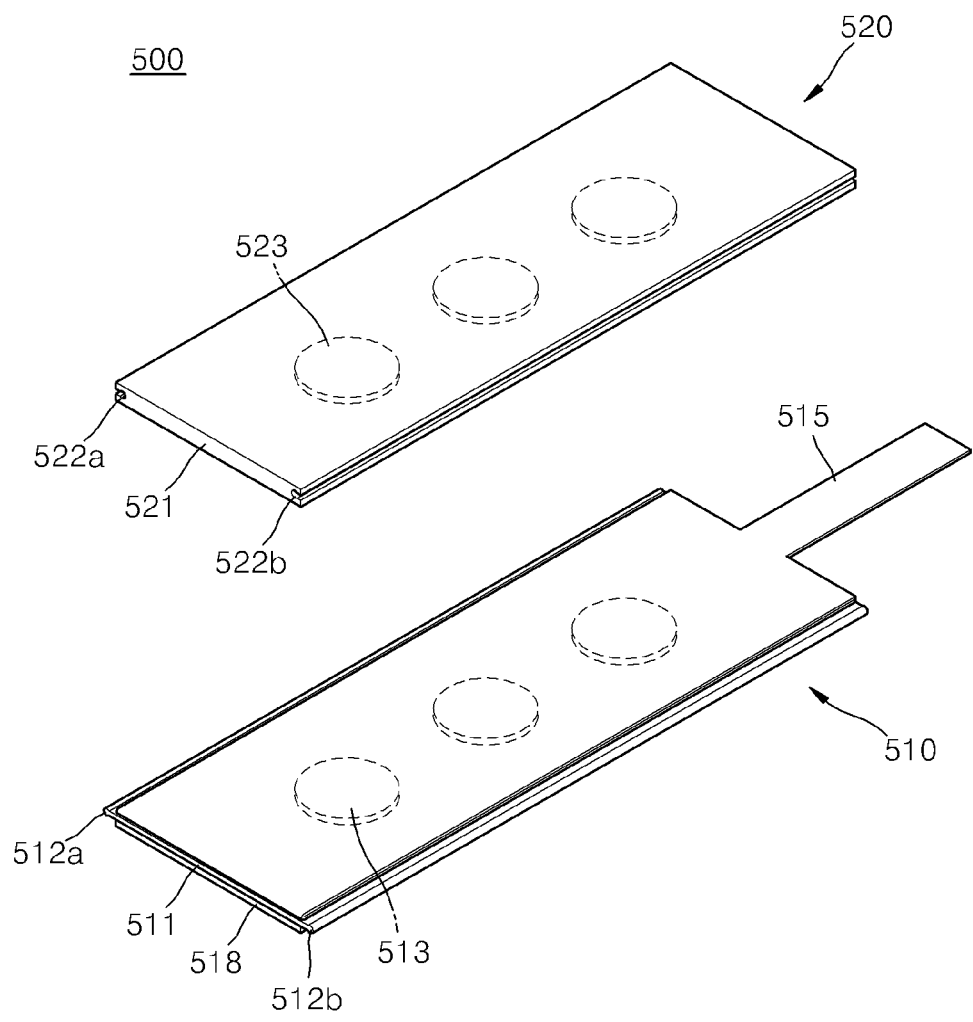
FIG. 14 is a diagram illustrating another example of a device for detecting bio-signals.

FIG. 14 illustrates another example of a device for detecting bio-signals. Referring to FIG. 14, the device for detecting bio-signals 500 includes an electrode for a living body 510 and a signal processing module 520. In this example, the electrode for a living body 510 includes an insulation sheet 511, guiding units 512a and 512b, an electrode unit 513, and first and second protection films 515 and 518. The signal processing module 520 includes a substrate 521, terminals 523 contacting the electrode unit 513 of the electrode for a living body 510, and module-side combining units 522a and 522b, which may be combined with the guiding units 512a and 512b. Components of the device for detecting bio-signals 500 other than structures for guiding and combining the electrode for a living body 510 and the signal processing module 520 are substantially the same as the corresponding components stated in the previous examples, and thus, further description thereof is omitted here.

In this example, the insulation sheet 511 has a rectangular shape, and may be formed of a nonconductive material or an insulation material. For example, the insulation sheet 511 may be formed of an insulation resin, an insulation fiber, paper, a combination thereof, and the like. For example, the guiding units 512a and 512b may extend from two opposite edges of the insulation sheet 511, and edges of the guiding units 512a and 512b may be convex zip fasteners. For example, the guiding units 512a and 512b may function as electrode-side combining units as well as guiding the signal processing unit 520 to be attached to an accurate location on the electrode for a living body 510.

The module-side combining units 522a and 522b, which may be concave zip fasteners corresponding to the guiding units 512a and 512b, may be formed at edges of the substrate 521 of the signal processing module 520. The shape of the guiding units 512a and 512b and the shape of the module-side combining units 522a and 522b may be reversed. In this example, the guiding units 512a and 512b may be folded inward from the two opposite edges of the insulation sheet 511, and locations of the guiding units 512a and 512b and the module-side combining units 522a and 522b may be determined in advance for precise alignment between the electrode unit 513 of the electrode for a living body 510 and the terminal 523 of the signal processing module 520.

Figure 15A:
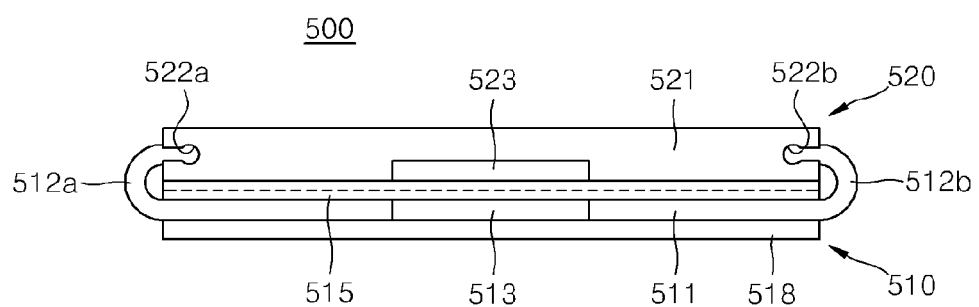
FIGS. 15A and 15B are diagrams illustrating examples of the device for detecting bio-signals of FIG. 14 in which a signal processing module is attached to an electrode for a living body.
Figure 15B:
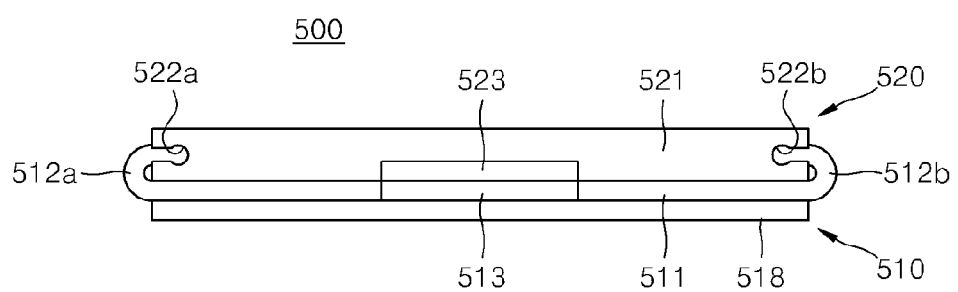

FIGS. 15A and 15B illustrate examples of the device for detecting bio-signals of FIG. 14 in which a signal processing module is attached to an electrode for a living body.

Referring to FIG. 15A, edges of the guiding units 512a and 512b of the electrode for a living body 510 are combined to the module-side combining units 522a and 522b of the signal processing module 520. In this example, the guiding units 512a and 512b not only guide the electrode unit 513 of the electrode for a living body 510 and the terminal 523 of the signal processing module 520 to be precisely aligned, but also stably attach the signal processing module 520 to the electrode for a living body 510. Next, while the signal processing module 520 is aligned with the guiding units 512*a* and 512*b* of the electrode for a living body 510, the first protection film 515 may be pulled and removed. Accordingly, when the first protection film 515 is removed from the electrode for a living body 510, the signal processing module 520 may directly contact and may be adhered to the electrode for a living body 510 as shown in FIG. 15B.

The examples of the electrodes for a living body and the devices for detecting bio-signals described herein may improve convenience for combining/detaching the electrodes and signal processing modules. Furthermore, when an electrode for a living body is attached to a signal processing module, the electrode for a living body and the signal processing module are electrically connected to each other via surface contact, and thus fine signals may be stably acquired.

It should be understood that the exemplary embodiments described herein should be considered in a descriptive sense only and not for purposes of limitation. Descriptions of features or aspects within each embodiment should typically be considered as available for other similar features or aspects in other embodiments.

The processes, functions, methods, and/or software described above may be recorded, stored, or fixed in one or more computer-readable storage media that includes program instructions to be implemented by a computer to cause a processor to execute or perform the program instructions. The media may also include, alone or in combination with the program instructions, data files, data structures, and the like. The media and program instructions may be those specially designed and constructed, or they may be of the kind well-known and available to those having skill in the computer software arts. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The described hardware devices may be configured to act as one or more software modules in order to perform the operations and methods described above, or vice versa. In addition, a computer-readable storage medium may be distributed among computer systems connected through a network and computer-readable codes or program instructions may be stored and executed in a decentralized manner.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An electrode to connect a living body to a signal processing module, the electrode comprising:
   an insulation sheet comprising at least one via hole;
   an electrode unit formed in the at least one via hole; and
   a guiding unit configured at an edge of the insulation sheet to guide an attachment of the signal processing module to the electrode for the living body,
   wherein an adhesive material is applied to regions of the insulation sheet around a device contacting portion of the electrode unit, the regions and the device contacting portion being configured to physically contact the signal processing module.

2. The electrode of claim 1, wherein the guiding unit comprises at least one protruding unit configured to guide the signal processing module to a location to which the signal processing module is to be attached.

3. The electrode of claim 1, wherein the guiding unit comprises an outer wall structure formed at edges of the insulation sheet.

4. The electrode of claim 1, wherein the guiding unit comprises an electrode-side combining unit configured to be combined with the signal processing module.

5. The electrode of claim 4, wherein the guiding unit comprises an end portion configured to be inserted into a slot of the signal processing module.

6. The electrode of claim 4, wherein the electrode-side combining unit comprises at least one of a zip fastener, a hook/loop fastener, and a flexible magnet.

7. The electrode of claim 4, wherein the guiding unit comprises a folded structure configured to guide the signal processing module to a location to which the signal processing module is to be attached.

8. The electrode of claim 1, wherein the electrode unit comprises:
   the device contacting portion that is formed of a conductive and adhesive material on a surface of the insulation sheet, and configured to contact a terminal of the signal processing module; and
   a body contacting portion that is formed on another surface of the insulation sheet and that is electrically connected to the device contacting portion.

9. A device to detect bio-signals, the device comprising:
   an electrode for a living body; and
   a signal processing module,
   wherein the electrode for the living body comprises
      an insulation sheet comprising at least one via hole,
      an electrode unit formed in the at least one via hole, and
      a guiding unit configured at an edge of the insulation sheet to guide an attachment of the signal processing module to the electrode,
   the signal processing module comprises a terminal corresponding to the electrode unit of the electrode, and
   an adhesive material is applied to regions of the insulation sheet around a device contacting portion of the electrode unit, the regions and the device contacting portion being configured to physically contact the signal processing module.

10. The device of claim 9, wherein the guiding unit comprises at least one protruding unit configured to guide the signal processing module to a location to which the signal processing module is to be attached.

11. The device of claim 9, wherein the guiding unit comprises an outer wall structure formed at edges of the insulation sheet.

12. The device of claim 9, wherein the guiding unit comprises a combining unit configured to combine the electrode for the living body and the signal processing module.

13. The device of claim 12, wherein the guiding unit comprises an inserting portion, and
   the signal processing module comprises a slot into which the inserting portion of the guiding unit is to be inserted.

14. The device of claim 12, wherein the combining unit comprises at least one of a zip fastener, a hook/loop fastener, and a flexible magnet.

15. The device of claim 12, wherein the guiding unit comprises a folded structure configured to guide the signal processing module to a location to which the signal processing module is to be attached.

16. The device of claim 9, wherein the electrode unit comprises:
   the device contacting portion that is formed of a conductive and adhesive material on a surface of the insulation sheet, and configured to contact the terminal of the signal processing module; and
   a body contacting portion that is formed on another surface of the insulation sheet and that is electrically connected to the device contacting portion.

17. The device of claim 9, wherein a silicon releasing agent is applied onto a surface of the signal processing module, and the surface of the signal processing module contacts the electrode for the living body.

18. The device of claim 9, wherein the signal processing module further comprises:
   an analog signal processing unit configured to process analog signals transmitted from the terminal;
   an analog to digital (A/D) converter configured to convert the analog signals to digital signals; and
   a digital signal processing unit configured to process the converted digital signals.

* * * * *